(12) United States Patent
Lou et al.

(10) Patent No.: US 9,877,695 B2
(45) Date of Patent: Jan. 30, 2018

(54) MODULATING X-RAY RADIATION DOSE IN CT SCAN

(71) Applicant: Shenyang Neusoft Medical Systems Co., Ltd., Shenyang (CN)

(72) Inventors: Shanshan Lou, Shenyang (CN); Liang Ren, Shenyang (CN); Ling Pang, Shenyang (CN)

(73) Assignee: SHENYANG NEUSOFT MEDICAL SYSTEMS CO., LTD., Shenyang (CN)

( * ) Notice: Subject to any disclaimer, the term of this patent is extended or adjusted under 35 U.S.C. 154(b) by 49 days.

(21) Appl. No.: 14/945,441

(22) Filed: Nov. 19, 2015

(65) Prior Publication Data

US 2016/0135777 A1    May 19, 2016

(30) Foreign Application Priority Data

Nov. 19, 2014  (CN) .......................... 2014 1 0665463
Nov. 16, 2015  (CN) .......................... 2015 1 0785038

(51) Int. Cl.
    *A61B 6/00*    (2006.01)
    *A61B 6/03*    (2006.01)

(52) U.S. Cl.
    CPC .............. *A61B 6/544* (2013.01); *A61B 6/032* (2013.01); *A61B 6/488* (2013.01); *A61B 6/583* (2013.01)

(58) Field of Classification Search
    CPC ........................... A61B 6/542; A61B 6/5205
    See application file for complete search history.

(56) References Cited

U.S. PATENT DOCUMENTS

| 5,379,333 | A   | 1/1995 | Toth |
| 5,400,378 | A   | 3/1995 | Toth |
| 6,198,789 | B1  | 3/2001 | Dafni |
| 6,404,844 | B1  | 6/2002 | Horiuchi et al. |
| 2004/0062341 | A1 | 4/2004 | Popescu et al. |
| 2007/0286332 | A1* | 12/2007 | Gohno .................. A61B 6/032 378/15 |
| 2008/0232542 | A1 | 9/2008 | Lin |

(Continued)

FOREIGN PATENT DOCUMENTS

| CN | 1496713 A    | 5/2004 |
| CN | 1942141 A    | 4/2007 |
| CN | 101084830 A  | 12/2007 |

(Continued)

*Primary Examiner* — Hoon Song
(74) *Attorney, Agent, or Firm* — Kilpatrick Townsend & Stockton LLP

(57) ABSTRACT

A method for modulating x-ray radiation dose in CT scan is disclosed. The method may include: acquiring x-ray attenuation information of each Z position within a planned scanning sequence for a scan region of a subject from data of a finished scanning sequence for the subject; and then, based on the acquired x-ray attenuation information, performing dose modulation with respect to the XY scanning profile at each Z position within the planned scanning sequence. The finished scanning sequence can be an axial and/or helical scanning sequence for a scan region wholly or partially same as the scan region and has been performed earlier. The Z position may include a position in Z direction extending from head to foot of the subject or conversely. The XY scanning profile may include a scanning profile of the subject which is vertical to Z direction.

16 Claims, 5 Drawing Sheets

101

X-ray attenuation information for each of different projection angles of the XY scanning profile at each of different Z positions within a planned scanning sequence with respect to a scan region of a subject may be acquired from data of a finished scanning sequence of the subject, and then the x-ray radiation dose for each projection angle of the XY scanning profile at each Z position within the planned scanning sequence may be modulated according to the acquired x-ray attenuation information.

(56) References Cited

U.S. PATENT DOCUMENTS

2014/0177782 A1* 6/2014 Herold ................... A61B 6/032
378/4

FOREIGN PATENT DOCUMENTS

| CN | 101283262 A | 10/2008 |
|---|---|---|
| CN | 102100562 A | 6/2011 |
| CN | 103494613 A | 1/2014 |
| CN | 104116518 A | 10/2014 |
| JP | 2012100692 A | 5/2012 |

* cited by examiner

101

X-ray attenuation information for each of different projection angles of the XY scanning profile at each of different Z positions within a planned scanning sequence with respect to a scan region of a subject may be acquired from data of a finished scanning sequence of the subject, and then the x-ray radiation dose for each projection angle of the XY scanning profile at each Z position within the planned scanning sequence may be modulated according to the acquired x-ray attenuation information.

FIG. 1 (Abstract Figure)

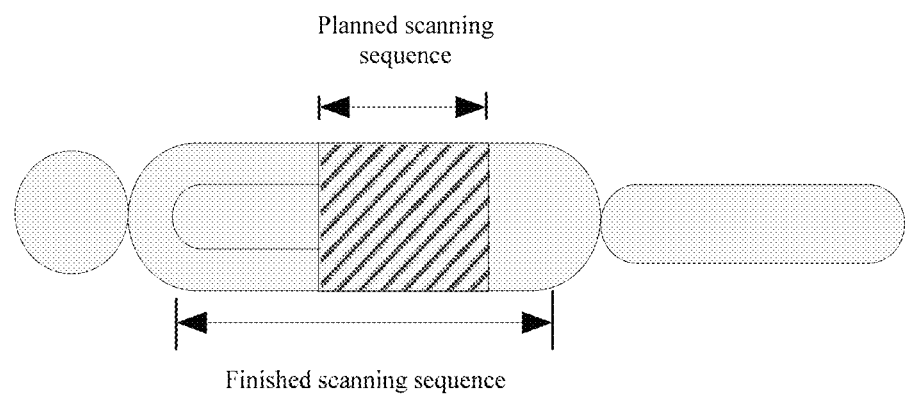

Shape scale ratio information of the XY scanning profile at each of different Z positions within an overlapping sequence may be acquired, and then, according to the acquired shape scale ratio information, it may determine whether the XY scanning profiles at different Z positions within the overlapping sequence are similar or not. Wherein, the overlapping sequence represents a part of the planned scanning sequence which is overlapped with the finished scanning sequence.

402

If it is determined that the XY scanning profiles at different Z positions within the overlapping sequence are similar, the maximum x-ray attenuation value for each of the projection angles of the XY scanning profile at each of Z positions within the planned scanning sequence may be acquired from data of the finished scanning sequence, and the x-ray radiation dose for each of the projection angles of the XY scanning profile at each of Z positions within the planned scanning sequence may be determined correspondingly.

FIG. 4

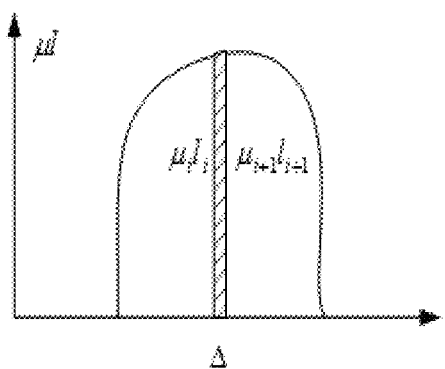

FIG. 5

MODULATING X-RAY RADIATION DOSE IN CT SCAN

The present application claims the priority to Chinese Patent Applications No. 201410665463.X, filed with the Chinese State Intellectual Property Office on Nov. 19, 2014, and Chinese Patent Applications No. 201510785038.9, filed with the Chinese State Intellectual Property Office on Nov. 16, 2015, both of which are incorporated herein by reference in their entireties.

BACKGROUND

The present disclosure relates to CT scan.

NEUSOFT MEDICAL SYSTEMS CO., LTD. (NMS), founded in 1998 with its world headquarters in China, is a leading supplier of medical equipment, medical IT solutions, and healthcare services. NMS supplies medical equipment with a wide portfolio, including CT, MRI, digital X-ray machine, Ultrasound, PET (Positron Emission Tomography), Linear Accelerator, and Biochemistry Analyser. Currently, NMS' products are exported to over 60 countries and regions around the globe, serving more than 5,000 renowned customers. NMS's latest successful developments, such as 128 Multi-Slice CT Scanner System, Superconducting MRI, Linear Accelerator, and PET products, have led China to become a global high-end medical equipment producer. As an integrated supplier with extensive experience in large medical equipment, NMS has been committed to the study of avoiding secondary potential harm caused by excessive X-ray irradiation to the subject (e.g., a patient) during the CT scanning process.

BRIEF DESCRIPTION OF DRAWINGS

Features of the present disclosure are illustrated by way of example and not limited in the following figure(s), in which like numerals indicate like elements, in which:

FIG. 1 is a flowchart of a method for modulating x-ray radiation dose in CT scan according to an example of the present disclosure;

FIG. 2 is a side view of a subject according to an example of the present disclosure;

FIG. 4 illustrates a schematic flowchart of a method for modulating x-ray radiation dose in CT scan according to an example of the present disclosure in which a planned scanning sequence goes beyond the range of a finished scanning sequence and has no abrupt change of a subject region in the Z-direction;

FIG. 5 schematically illustrates a slice data in an example of the present disclosure;

DETAILED DESCRIPTION

Figure 3A:
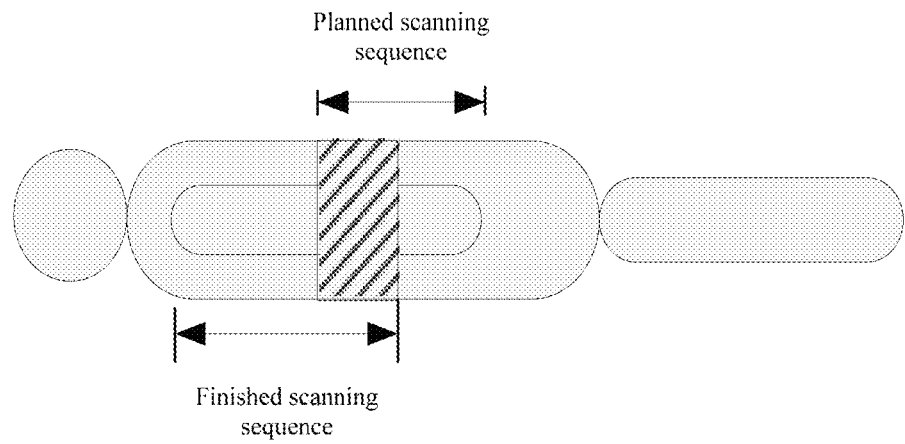
FIG. 3A and FIG. 3B are side views of a subject according other examples of the present disclosure.

For simplicity and illustrative purposes, the present disclosure is described by referring mainly to an example thereof. In the following description, numerous specific details are set forth in order to provide a thorough understanding of the present disclosure. It will be readily apparent however, that the present disclosure may be practiced without limitation to these specific details. In other instances, some methods and structures have not been described in detail so as not to unnecessarily obscure the present disclosure. As used herein, the terms "a" and "an" are intended to denote at least one of a particular element, the term "includes" means includes but not limited to, the term "including" means including but not limited to, and the term "based on" means based at least in part on.

Computed Tomography (CT) is a widely used medical technology, in which, however, different methods for modulating x-ray radiation dose may directly influence the quality of a reconstructed CT image, and may even cause serious damages to the subject due to excessive irradiation.

Usually, for a method for modulating x-ray radiation dose in CT scan, according to the physical size or profile of a subject and information about X-ray attenuation at different positions in Z direction (an anatomically defined vertical axis), the scan slices of the subject at different positions in Z direction may be approximated as an ellipse, wherein the length ratio between the long axis and the short axis of the ellipse may be set empirically. However, due to factors such as individual difference of subjects, the above approximation may be inaccurate and lead to an excessive or excessively small dose, which may negatively influence the quality of the reconstructed CT image or even cause severe damages to the subjects due to excessive irradiation.

FIG. 1 is a flowchart illustrating a method for modulating x-ray radiation dose in CT scan according to an example of the present disclosure. The method may include the following block 101.

At block 101, x-ray attenuation information for each of different projection angles of the XY scanning profile at each of different Z positions within a planned scanning sequence with respect to a scan region of a subject may be acquired. The x-ray attenuation information can be acquired from data of a finished scanning sequence of the subject, and the x-ray radiation dose for each projection angle of the XY scanning profile at each Z position within the planned scanning sequence may be modulated according to the acquired x-ray attenuation information, wherein, Z position may include a position in Z direction from head to foot of the subject or conversely, and the XY scanning profile may include a scanning profile of the subject which is vertical to Z direction.

In examples of the present disclosure, the x-ray attenuation information of a planned scanning sequence for current scan region of a subject may be acquired from data of some finished axial and/or helical scanning sequence of the subject, and a x-ray radiation dose modulation with respect to the XY scanning profile at each of Z positions within the planned scanning sequence may be performed based on the acquired x-ray attenuation information. The finished axial and/or helical scanning sequence may include the axial and/or helical scanning sequence for the same scan region of the same subject which has been finished before the current time, and may be referred to as "finished scanning sequence" hereinafter. As long as the x-ray attenuation information with respect to the scan region of the subject is acquired, an x-ray dose modulation may be performed based on the x-ray attenuation information. This may guarantee noise consistency between reconstructed CT images for different scan regions of a same subject.

In examples of the present disclosure, the planned scanning sequence may be within or beyond the range of the finished scanning sequence. The following description of a method for modulating x-ray radiation dose in CT scan is given with respect to these two different relationships between the planned scanning sequence and the finished scanning sequence respectively.

FIG. 2 illustrates a side view of a subject. When the range of the planned scanning sequence is within the range of the finished scanning sequence, the x-ray attenuation information for each of different projection angles of the XY scanning profile at each of different Z positions within the planned scanning sequence may be acquired based on a corresponding relationship between the finished scanning sequence and the planned scanning sequence, and then an x-ray dose modulation may be performed based on the acquired x-ray attenuation information.

Particularly, if the range of the planned scanning sequence is within the range of the finished scanning sequence, a x-ray radiation dose $I_{mod,zi,j}$ for the $j^{th}$ projection angle of the XY scanning profile at a Z position zi within the planned scanning sequence may be calculated according to the following equation:

$$I_{mod,zi,j} = \frac{M \cdot I_{mod,zi,start}}{\sum_{j=1}^{M} \sqrt{A_{max,zi,j}}} \cdot \sqrt{A_{max,zi,j}} \quad (1)$$

wherein, $I_{mod,zi,start}$ represents an initial x-ray radiation dose of Z position zi, which may be calculated through equation (17) described below, M represents a quantity of projection angles, and j represents an index number of the $j^{th}$ projection angle, $A_{max,zi,j}$ represents a maximum x-ray attenuation value for the $j^{th}$ projection angle of the XY scanning profile at Z position zi in the data of the finished scanning sequence, and represents the maximum of the x-ray attenuation values which are calculated based on the X-ray attenuation signals detected by each of the detection channels of the CT scanner respectively.

Figure 3B:
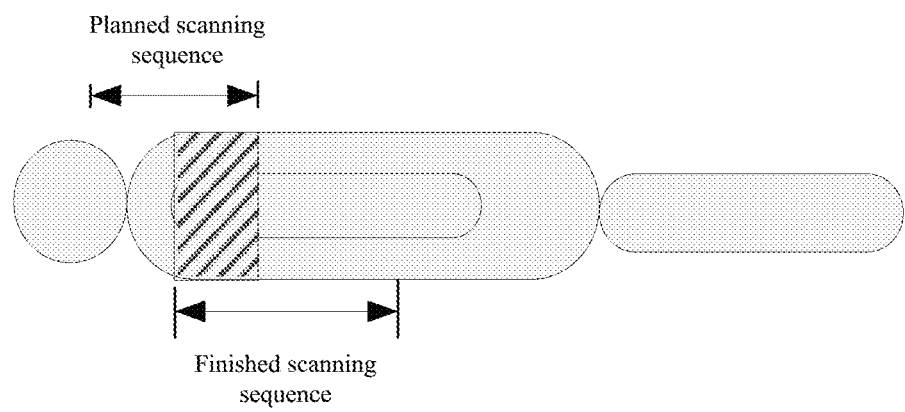

FIG. 3A and FIG. 3B illustrate side views of a subject, and a difference between FIG. 3A and FIG. 3B is: in FIG. 3A, when pilot image data of the planned scanning sequence does not have any abrupt change in Z direction; and in FIG. 3B, when pilot image data of the planned scanning sequence may have an abrupt change in Z direction such as from neck to shoulder or conversely. When the range of the planned scanning sequence goes beyond the range of the finished scanning sequence, it is to further determine whether the pilot image data of the planned scanning sequence may have an abrupt change in Z direction. The following description is mainly directed to a case where the pilot image data of the planned scanning sequence has no abrupt change in Z direction.

Specifically, when the range of the planned scanning sequence goes beyond the range of the finished scanning sequence and the pilot image data of the planned scanning sequence has no abrupt change in Z direction, referring to FIG. 4, operation(s) described in block 101 shown in FIG. 1 can be performed. FIG. 4 illustrates, in some examples in accordance with the present disclosure, block 101 can comprise the following blocks 401 and 402.

At block 401, shape ratio information of the XY scanning profile at each of different Z positions within an overlapping sequence may be acquired, and then, according to the acquired shape ratio information, it may be determined whether the XY scanning profiles at different Z positions within the overlapping sequence are similar to each other or not, wherein the overlapping sequence represents a part of the planned scanning sequence which is overlapped with the finished scanning sequence.

For example, by calculating the x-ray attenuation information for each of the different projection angles of the XY scanning profile at each of Z positions within the overlapping sequence, the shape ratio information of the XY scanning profile at each of Z positions within the overlapping sequence may be acquired according to the calculated x-ray attenuation information; and then, according to the acquired shape ratio information, it may be determined whether the XY scanning profiles at different Z positions are similar each other or not, and if yes, a x-ray dose modulation may be performed subsequently, and if not, the procedure not perform the x-ray does modulation.

In an example, according to the x-ray attenuation information of the overlapping sequence (including the x-ray attenuation information for each of different projection angles of the XY scanning profile at each of Z positions) acquired from the data of the finished scanning sequence, the equivalent circular water phantom at each of Z positions within the overlapping sequence may be converted into an equivalent elliptical water phantom of the same area.

For any Z position, the following equation may hold:

$$S_{Circle,pzi} = \pi \cdot (D_{zi}/2)^2 = \pi \cdot \frac{a_{Ellipse,pzi}}{2} \cdot \frac{b_{Ellipse,pzi}}{2} = S_{Ellipse,pzi} \quad (2)$$

wherein, $S_{Circle,pzi}$ represents an area of the equivalent circular water phantom at the $i^{th}$ Z position Pzi within the overlapping sequence, $S_{Ellipse,pzi}$ represents an area of the equivalent elliptical water phantom at the $i^{th}$ Z position Pzi within the overlapping sequence, $D_{zi}$ represents the diameter of the equivalent circular water phantom at the $i^{th}$ Z position Pzi within the overlapping sequence, which can be calculated through equation (18) described below, $a_{Ellipse,pzi}$ and $b_{Ellipse,pzi}$ respectively represent a length of the long axis and a short axis of the equivalent elliptical water phantom at the $i^{th}$ Z position Pzi within the overlapping sequence. In some examples, length of the long axis $a_{Ellipse,pzi}$ may be set according to the maximum of water phantom x-ray attenuation values which are converted from the x-ray attenuation value for each of different projection angles of the XY scanning profile at the $i^{th}$ Z position Pzi in the data of the finished scanning sequence, and length of the short axis $b_{Ellipse,pzi}$ can be calculated through the above equation (2).

The shape ratio information $\delta_{pzi}$ of the XY scanning profile at the $i^{th}$ Z position Pzi may be acquired by calculating the ratio between the long axis and the short axis of the equivalent elliptical water phantom at the $i^{th}$ Z position Pzi. For example, it may be calculated through the following equation (3).

$$\delta_{pzi} = \frac{a_{Ellipse,pzi}}{b_{Ellipse,pzi}} \quad (3)$$

By calculating an arithmetic mean for the shape ratio information $\delta_{pzi}$ of the XY scanning profile at each of all Z positions Pzi within the overlapping sequence, i.e., substituting the equation (3) into the following equation (4), a mean shape ratio information $\delta_{mean}$ of the overlapping sequence may be acquired:

$$\delta_{mean} = \frac{1}{NumZ} \sum_{i=1}^{NumZ} \delta_{pzi} \quad (4)$$

wherein, i=1, 2, . . . NumZ, NumZ represents a quantity of all Z positions within the overlapping sequence.

By calculating a variance with the shape ratio information $\delta_{pzi}$ of the XY scanning profile at each of all Z positions Pzi within the overlapping sequence and the mean shape ratio information $\delta_{mean}$ of the overlapping sequence, i.e., substituting the equations (3) and (4) into the following equation (5), a variance regarding shape ratio information D1 of the overlapping sequence can be calculated:

$$D1 = \frac{1}{NumZ} \sum_{i=1}^{NumZ} (\delta_{pzi} - \delta_{mean})^2, i = 1, 2, \ldots NumZ \quad (5)$$

If the variance regarding shape ratio information D1 of the overlapping sequence is larger than a preset threshold value T1, it may be determined that the XY scanning profiles at different Z positions within the overlapping sequence are not similar and the supposed subsequent operation may be omitted. If the variance regarding shape ratio information D1 is equal or less than the threshold value T1, it may be determined that the XY scanning profiles at different Z positions within the overlapping sequence are similar, wherein, the threshold value T1 may be set arbitrarily according to practical application scenarios.

Based on the above, block 401 may include:

converting the equivalent circular water phantom for the XY scanning profile at each of Z positions within the overlapping sequence into an equivalent elliptical water phantom of the same area;

calculating, with the above equation (3), the length ratio between the long axis and the short axis of the equivalent elliptical water phantom at each of Z positions within the overlapping sequence, as the shape ratio information $\delta_{pzi}$ of the XY scanning profile at each of Z positions within the overlapping sequence;

calculating, with the above equations (4) and (5), the variance regarding shape ratio information D1 of the overlapping sequence; and determining whether the variance regarding shape ratio information D1 is larger than a preset threshold value T1, and if yes, it may indicate that the XY scanning profiles at different Z positions within the overlapping sequence are not similar; and if no, it may indicate that the XY scanning profiles at different Z positions within the overlapping sequence are similar.

In other examples, since the x-ray attenuation value at each of Z positions zi mainly depends on the shape and x-ray attenuation coefficient of the XY scanning profile at Z position zi, the x-ray attenuation deviation of each of Z positions zi with respect to the whole overlapping sequence may be calculated as the shape ratio information of the XY scanning profile at Z position zi. For example, for any Z position zi within the overlapping sequence, by calculating an arithmetic mean for the absolute value of the difference between a maximum x-ray attenuation value for each of the projection angles at Z position zi and the mean maximum x-ray attenuation value for corresponding projection angle of the whole overlapping sequence, an x-ray attenuation deviation of Z position zi with respect to the whole overlapping sequence may be acquired.

Further, the maximum x-ray attenuation value for each of the projection angles may be normalized so as to simplify related calculations. For example, for any Z position zi within the overlapping sequence, the maximum x-ray attenuation value for each of the projection angles may be normalized by the maximum x-ray attenuation value in pilot image scanning of the XY scanning profile at Z position zi or the diameter of the equivalent circular water phantom for the XY scanning profile at Z position zi, and thus a normalized x-ray attenuation value for each of the projection angles of the XY scanning profile at Z position zi may be acquired.

Specifically, according to an example, a maximum x-ray attenuation value $A_{max,zi,j}$ for each of the projection angles j of the XY scanning profile at each of Z positions zi within the overlapping sequence may be acquired from data of the finished scanning sequence, a maximum x-ray attenuation value in pilot image scanning $PA_{max,zi}$ of the XY scanning profile at each of Z positions zi may be acquired from pre-acquired pilot image data of the subject, and then a maximum x-ray attenuation value $A_{max,zi,j}$ for each of the projection angles j of the XY scanning profile at each of Z positions zi within the overlapping sequence may be normalized by a maximum x-ray attenuation value in pilot image scanning $PA_{max,zi}$ of the XY scanning profile at each of Z positions zi, so as to acquire a normalized x-ray attenuation value $C_{mod,zi,j}$ for each of the projection angles of the XY scanning profile at each of Z positions zi within the overlapping sequence, specifically expressed as follows:

$$C_{mod,zi,j} = \frac{A_{max,zi,j}}{PA_{max,zi}} \quad (6)$$

wherein, i=1, 2, . . . NumZ, j=1, 2 . . . M, $A_{max,zi,j}$ represents a maximum x-ray attenuation value for the $j^{th}$ projection angle of the XY scanning profile at the $i^{th}$ Z position zi within the overlapping sequence, $P_{max,zi}$ represents a maximum x-ray attenuation value in pilot image scanning of the XY scanning profile at the $i^{th}$ Z position zi and may be determined from pre-acquired pilot image data of the subject, NumZ represents a quantity of Z positions within the overlapping sequence, and i represents an index number of the $i^{th}$ Z position, and M represents a quantity of projection angles, and j represents an index number of the $j^{th}$ projection angle.

By calculating an arithmetic mean for the normalized x-ray attenuation value $C_{max,zi,j}$ for the $j^{th}$ projection angle of each of Z positions zi within the overlapping sequence, a mean normalized x-ray attenuation value $\overline{C_{mod,j}}$ for the $j^{th}$ projection angle of the overlapping sequence may be acquired, specifically expressed as follows:

$$\overline{C_{mod,j}} = \frac{\sum_{i=1}^{NumZ} C_{mod,zi,j}}{NumZ} \tag{7}$$

By calculating an arithmetic mean for the absolute value of the difference between the normalized x-ray attenuation value $C_{max,zi,j}$ for each of the projection angles of the XY scanning profile at each of Z positions zi within the overlapping sequence and the mean normalized x-ray attenuation value $\overline{C_{mod,j}}$ for the corresponding projection angle of the overlapping sequence, an x-ray attenuation deviation $\Delta C_{mod,zi}$ of each of Z positions zi within the overlapping sequence may be acquired, specifically expressed as follows:

$$\Delta C_{mod,zi} = \frac{\sum_{j=1}^{M} |C_{mod,zi,j} - \overline{C_{mod,j}}|}{M} \tag{8}$$

By calculating an arithmetic mean for the x-ray attenuation deviation $\Delta C_{mod,zi}$ of each of Z positions zi within the overlapping sequence, a mean x-ray attenuation deviation $\Delta C_{mean}$ of the overlapping sequence may be acquired, specifically expressed as follows:

$$\Delta C_{mean} = \frac{1}{NumZ} \sum_{i=1}^{NumZ} \Delta C_{mod,zi} \tag{9}$$

By calculating a variance with the x-ray attenuation deviation $\Delta C_{mod,zi}$ of each of Z positions zi within the overlapping sequence and the mean x-ray attenuation deviation $\Delta C_{mean}$ of the overlapping sequence, that is, substituting the equations (8) and (9) into the following equation (10), a variance regarding x-ray attenuation deviation D2 of the overlapping sequence may be acquired:

$$D2 = \frac{1}{NumZ} \sum_{i=1}^{NumZ} (\Delta C_{mod,zi} - \Delta C_{mean})^2, \tag{10}$$

$$i = 1, 2, \ldots NumZ, j = 1, 2, \ldots M$$

If the variance regarding x-ray attenuation deviation D2 of the overlapping sequence is larger than a preset threshold value T2, it may be determined that the XY scanning profiles at different Z positions within the overlapping sequence are not similar and the supposed subsequent operation can be omitted. If the variance regarding x-ray attenuation deviation D2 of the overlapping sequence is equal or less than the threshold value T2, it may be determined that the XY scanning profiles at different Z positions within the overlapping sequence are similar. The threshold value T2 may be set arbitrarily according to practical application scenarios.

Based on the above, block 401 may include:

acquiring, from data of the finished scanning sequence, a maximum x-ray attenuation value $A_{max,zi,j}$ for each of the projection angles j of the XY scanning profile at each of Z positions zi within the overlapping sequence, acquiring, from pilot image data acquired beforehand, a maximum x-ray attenuation value $PA_{max,zi}$ of the XY scanning profile at each of Z positions zi in pilot image scanning, normalizing, according to the above equation (6), a maximum x-ray attenuation value $A_{max,zi,j}$ for each of the projection angles j of the XY scanning profile at each of Z positions zi within the overlapping sequence with a maximum x-ray attenuation value in pilot image scanning $PA_{max,zi}$ of the XY scanning profile at each of Z positions zi, so as to acquire a normalized x-ray attenuation value $C_{mod,zi,j}$ for each of the projection angles of the XY scanning profile at each of Z positions zi within the overlapping sequence;

calculating, according to the above equations (7) and (8), the x-ray attenuation deviation $\Delta C_{mod,zi}$ of each of Z positions zi within the overlapping sequence with the normalized x-ray attenuation value $C_{mod,z,j}$ for each of the projection angles of the XY scanning profile at each of Z positions zi within the overlapping sequence;

calculating, according to the equations (9) and (10), the mean x-ray attenuation deviation $\Delta C_{mean}$ of the overlapping sequence and the variance regarding x-ray attenuation deviation D2 of the overlapping sequence, with the x-ray attenuation deviation $\Delta C_{mod,zi}$ of each of Z positions zi within the overlapping sequence; and determining whether the variance regarding x-ray attenuation deviation D2 of the overlapping sequence is larger than a preset second threshold value T2, and if yes, it may indicate that the XY scanning profiles at different Z positions within the overlapping sequence are not similar, and if no, it may indicate that the XY scanning profiles at different Z positions within the overlapping sequence are similar.

According to another example of the present disclosure, a maximum x-ray attenuation value $A_{max,zi,j}$ for each of the projection angles j of the XY scanning profile in each of Z positions zi within the overlapping sequence may be acquired from data of the finished scanning sequence, the diameter $D_{zi}$ of the equivalent circular water phantom at each of Z positions zi within the overlapping sequence may be acquired from pilot image data obtained by a pilot image scanning beforehand, and then a maximum x-ray attenuation value $A_{max,zi,j}$ for each of the projection angles j of the XY scanning profile at each of Z positions zi within the overlapping sequence may be normalized by the diameter $D_{zi}$ of the equivalent circular water phantom at each of Z positions zi within the overlapping sequence, so as to acquire a normalized x-ray attenuation value $B_{mod,zi,j}$ for each of the projection angles of the XY scanning profile at each of Z positions zi within the overlapping sequence, specifically expressed as follows:

$$B_{mod,zi,j} = \frac{A_{max,zi,j}}{D_{Zi}} \tag{11}$$

wherein, $1 = 1, 2 \ldots NumZ$, $j=1, 2 \ldots M$, $A_{max,zi,j}$ represents a maximum x-ray attenuation value for the $j^{th}$ projection angle of the XY scanning profile at the $i^{th}$ Z position zi within the overlapping sequence, $D_{zi}$ represents the diameter of the equivalent circular water phantom of the XY scanning profile at the $i^{th}$ Z position zi within the overlapping sequence and may be calculated according to equation (18) described below;

NumZ represents a quantity of Z positions within the overlapping sequence, and i represents an index number of the $i^{th}$ Z position, and M represents a quantity of projection angles, and j represents an index number of the $j^{th}$ projection angle.

By calculating an arithmetic mean for the normalized x-ray attenuation value $B_{mod,zi,j}$ for the $j^{th}$ projection angle of each of Z positions zi within the overlapping sequence, a mean normalized x-ray attenuation value $\overline{B_{mod,j}}$ for the $j^{th}$ projection angle of the overlapping sequence may be acquired, specifically expressed as follows:

$$\overline{B_{mod,j}} = \frac{\sum_{i=1}^{NumZ} B_{mod,zi,j}}{NumZ} \quad (12)$$

By calculating an arithmetic mean for the absolute value of the difference between the normalized x-ray attenuation value $B_{mod,zi,j}$ for each of the projection angles of the XY scanning profile at each of Z positions zi within the overlapping sequence and the mean normalized x-ray attenuation value $\overline{B_{mod,j}}$ for the corresponding projection angle of the overlapping sequence, an x-ray attenuation deviation $\Delta B_{mod,zi}$ of each of Z positions zi within the overlapping sequence may be acquired, specifically expressed as follows:

$$\Delta B_{mod,zi} = \frac{\sum_{j=1}^{M} |B_{mod,zi,j} - \overline{B_{mod,j}}|}{M} \quad (13)$$

By calculating an arithmetic mean for the x-ray attenuation deviation $\Delta B_{mod,zi}$ of each of Z positions zi within the overlapping sequence, a mean x-ray attenuation deviation $\Delta B_{mean}$ of the overlapping sequence may be acquired, specifically expressed as follows:

$$\Delta B_{mean} = \frac{1}{NumZ} \sum_{i=1}^{NumZ} \Delta B_{mod,zi} \quad (14)$$

By calculating a variance with the x-ray attenuation deviation $\Delta B_{mod,zi}$ of each of Z positions zi within the overlapping sequence and the mean x-ray attenuation deviation $\Delta B_{mean}$ of the overlapping sequence, that is, substituting the equations (13) and (14) into the following equation (15), a variance regarding x-ray attenuation deviation D3 of the overlapping sequence may be acquired:

$$D3 = \frac{1}{NumZ} \sum_{i=1}^{NumZ} (\Delta B_{mod,zi} - \Delta B_{mean})^2, \quad (15)$$

$$i = 1, 2, \ldots NumZ, j = 1, 2, \ldots M$$

If the variance regarding x-ray attenuation deviation D3 of the overlapping sequence is larger than a preset threshold value T3, it may be determined that the XY scanning profiles at different Z positions within the overlapping sequence are not similar and the supposed subsequent operation may be omitted. If the variance regarding x-ray attenuation deviation D3 of the overlapping sequence is equal or less than the threshold value T3, it may be determined that the XY scanning profiles at different Z positions within the overlapping sequence are similar. The threshold value T3 may be set arbitrarily according to practical application scenarios.

Based on the above, block 401 may include:

acquiring, from data of the finished scanning sequence, a maximum x-ray attenuation value $A_{max,zi,j}$ for each of the projection angles j of the XY scanning profile at each of Z positions zi within the overlapping sequence, acquiring, from pilot image data acquired beforehand, the diameter $D_{zi}$ of the equivalent circular water phantom at each of Z positions zi within the overlapping sequence, normalizing, according to the above equation (11), a maximum x-ray attenuation value $A_{max,zi,j}$ for each of the projection angles j of the XY scanning profile at each of Z positions zi within the overlapping sequence, so as to acquire a normalized x-ray attenuation value $B_{mod,zi,j}$ for each of the projection angles of the XY scanning profile at each of Z positions zi within the overlapping sequence;

calculating, according to the above equations (12) and (13), the x-ray attenuation deviation $\Delta B_{mod,zi}$ of each of Z positions zi within the overlapping sequence with the normalized x-ray attenuation value $B_{mod,zi,j}$ for each of the projection angles of the XY scanning profile at each of Z positions zi within the overlapping sequence;

calculating, with the x-ray attenuation deviation $\Delta B_{mod,zi}$ of each of Z positions zi within the overlapping sequence, according to the equations (14) and (15), the mean x-ray attenuation deviation $\Delta B_{mean}$ of the overlapping sequence and the variance regarding x-ray attenuation deviation D3 of the overlapping sequence; and determining whether the variance regarding x-ray attenuation deviation D3 of the overlapping sequence is larger than a preset third threshold value T3, and if yes, it may indicate that the XY scanning profiles at different Z positions within the overlapping sequence are not similar, and if no, it may indicate that the XY scanning profiles at different Z positions within the overlapping sequence are similar.

At block 402, if it is determined that the XY scanning profiles at different Z positions within the overlapping sequence are similar to each other, a maximum x-ray attenuation value for each of the projection angles of the XY scanning profile at each of Z positions within the planned scanning sequence may be acquired from data of the finished scanning sequence, and the x-ray radiation dose for each of the projection angles of the XY scanning profile at each of Z positions within the planned scanning sequence may be determined correspondingly.

According to an example, first, a maximum x-ray attenuation value for each of the projection angles of the XY scanning profile at each of Z positions within the planned scanning sequence may be acquired from data of the finished scanning sequence; and then, according to the acquired maximum x-ray attenuation values, the x-ray radiation dose $I_{mod,j}$ for each of the projection angles of the XY scanning profile at each of Z positions within the planned scanning sequence may be determined.

Specifically, the x-ray radiation dose $I_{mod,zi,j}$ for the $j^{th}$ projection angle of the XY scanning profile at a Z position zi within the planned scanning sequence may be calculated according to the following equation:

$$I_{mod,zi,j} = \qquad (16)$$

$$\begin{cases} T_{max}, & \text{mod}v \geq T_{max} \\ \text{mod}v = \dfrac{M \cdot I_{mod,zi,start}}{\sum\limits_{j=1}^{M} \sqrt{A_{max,zi,j}}} \cdot \sqrt{A_{max,zi,j}}, & T_{min} \leq \text{mod}v \leq T_{max} \\ T_{min}, & \text{mod}v \leq T_{min} \end{cases}$$

wherein, $I_{mod,zi,start}$ represents the initial x-ray radiation dose corresponding to Z position zi, M represents a quantity of projection angles, j represents an index number of the $j^{th}$ projection angle, $A_{max,zi,j}$ represents a maximum x-ray attenuation value for the $j^{th}$ projection angle of the XY scanning profile at Z position zi, $T_{max}$ and $T_{min}$ represent a maximum x-ray dose threshold value and a minimum x-ray dose threshold value respectively, and mod v represents an x-ray intermediate value for comparing with $T_{max}$ and $T_{min}$ to determine the $I_{mod,zi,j}$.

According to an example, when a Z position zin within the planned scanning sequence is within the overlapping sequence too, a maximum x-ray attenuation value $A_{max,zi,j}$ for the $j^{th}$ projection angle of the XY scanning profile at Z position zin may be directly acquired from data of the finished scanning sequence. However, when a Z position zout within the planned scanning sequence is beyond the overlapping sequence, a maximum x-ray attenuation value $A_{max,zout,j}$ for the $j^{th}$ projection angle of the XY scanning profile at Z position zout may be predicted from the x-ray attenuation information in pilot image scanning of the XY scanning profile at Z position zout and the x-ray attenuation information of the XY scanning profile at another Z position zout−1 which is closest to the position zout, specifically as follows:

$$A_{max,zout,j} = A_{max,zout-1,j} \dfrac{PA_{max,zout}}{PA_{max,zout-1}} \qquad (16\text{-}1)$$

wherein, $A_{max,zout,j}$ represents a maximum x-ray attenuation value for the $j^{th}$ projection angle of the XY scanning profile at Z position zout;

$A_{max,zout-1,j}$ represents a maximum x-ray attenuation value for the $j^{th}$ projection angle of the XY scanning profile at Z position zout−1, which may be directly acquired from data of the finished scanning sequence or predicted using the above equation (16-1);

$PA_{max,zout}$ represents a maximum x-ray attenuation value in pilot image scanning of the XY scanning profile at Z position zout and may be determined from pre-acquired pilot image data of the subject;

$PA_{max,zout-1}$ represents a maximum x-ray attenuation value in pilot image scanning of the XY scanning profile at Z position zout−1 and may be determined from pre-acquired pilot image data of the subject.

According to an example, supposing the diameter of the equivalent circular water phantom at Z position zi within the planned scanning sequence is $D_{scan,zi}$, and the diameter of the reference equivalent water phantom of the CT scanner system is $D_{ref}$, the initial x-ray radiation dose $I_{mod,zi,start}$ of Z position zi may be determined by searching a table of x-ray dose recommendation function based on $D_{scan,zi}$ and $D_{ref}$.

In other words, the initial radiation x-ray dose $I_{mod,zi,start}$ may be set according to the following equation:

$$I_{mod,zi,start} = f(D_{scan,zi}, D_{ref}) \qquad (17)$$

wherein, $f(D_{scan,zi}, D_{ref})$ is a x-ray dose recommendation function;

$D_{scan,zi}$ represents the diameter of the equivalent circular water phantom at Z position zi within the planned scanning sequence, which may be calculated through the following equation (18);

$D_{ref}$ represents the diameter of the reference equivalent water phantom of the CT scanner system.

According to an example, a maximum x-ray dose threshold value $T_{max}$ and a minimum x-ray dose threshold value $T_{min}$ may be determined as follows.

Firstly, before block 101, a pilot image scanning is performed on the subject so as to acquire pilot image data of the subject, and then according to the acquired pilot image data, the diameter of the equivalent circular water phantom at each of Z positions may be determined. Wherein, the pilot image data of the subject usually comprises multiple sets of slice data. In other words, the XY scanning profile at each of Z positions corresponds to a set of slice data, and the diameter of the equivalent circular water phantom at Z position may be calculated with the set of slice data.

Referring to the schematic diagram of slice data as shown in FIG. 5, if a set of slice data is:

$$\{\mu_1 l_1, \mu_2 l_2, \ldots, \mu_i l_i\}, \; i=1,2,3,\ldots,N,$$

wherein, $\mu_i$ represents the mean x-ray attenuation coefficient of the $i^{th}$ detection channel, $l_i$ represents the length of the x-ray attenuation path in the $i^{th}$ detection channel, N represents a quantity of detection channels for the CT scanner system.

Then the diameter of the equivalent circular water phantom corresponding to the set of slice data may be calculated through the following equation:

$$D_{water} = \dfrac{2}{\mu_{water}} \cdot \sqrt{\dfrac{S}{\pi}} \qquad (18)$$

wherein, $\mu_{water}$ represents the x-ray attenuation coefficient of water,

S represents the x-ray attenuation area of the equivalent circular water phantom corresponding to the set of slice data.

According to an example, the x-ray attenuation area S of the equivalent circular water phantom corresponding to a set of slice data may be calculated as follows:

$$S = \sum_{i=1}^{N} (\mu_i l_i + \mu_{i+1} l_{i+1}) \cdot \Delta/2 \qquad (19)$$

$$\Delta = R \cdot \dfrac{\theta}{N} \cdot g(h_{bed}, h_{center}) \qquad (19\text{-}1)$$

wherein, Δ represents the distance between the centres of adjacent detection units (detectors), R represents the radius of rotation, θ represents the sector angle formed between the detection units and the bulb tube, N represents a quantity of detection channels for the CT scanner system, $h_{bed}$ represents the distance between the scanning bed and the floor, $h_{center}$ represents the distance between the centre of rotation and the floor;

$g(h_{bed}, h_{center})$ represents a function for modifying Δ. When the subject is located at the centre of rotation, $g(h_{bed}, h_{center})=1$; when the subject is located above the centre of rotation, $g(h_{bed}, h_{center})<1$; and when the subject is located below the centre of rotation, $g(h_{bed}, h_{center})>1$. The specific value of $g(h_{bed}, h_{center})$ may be obtained by searching the table of modification function.

Then, for the diameters of equivalent circular water phantom calculated from multiple sets of slice data which is contained in the pilot image data of the subject, a maximum and a minimum of them are respectively selected as a maximum equivalent circular water phantom diameter $D_{max}$ and a minimum equivalent circular water phantom diameter $D_{min}$ respectively, and Z position of the XY scanning profile having a maximum equivalent circular water phantom diameter $D_{max}$ (hereafter referred as "maximum profile position $P_{max}$") and Z position $P_{min}$ of the XY scanning profile having a minimum equivalent circular water phantom diameter $D_{min}$ (hereafter referred as "minimum profile position $P_{min}$") are determined correspondingly.

Next, the equivalent circular water phantom at a maximum profile position $P_{max}$ may be converted into an equivalent water phantom of the same area, and the equivalent circular water phantom at a minimum profile position $P_{min}$ may be converted into an equivalent water phantom of the same area also.

According to an example, with the above equation (19), the x-ray attenuation area S1 of the equivalent circular water phantom at a maximum profile position $P_{max}$ may be calculated based on the slice data which is contained in the pilot image data of the subject which corresponds to a maximum profile position $P_{max}$. Similarly, based on the slice data corresponding to a minimum profile position $P_{min}$, an x-ray attenuation area S2 of the equivalent circular water phantom at a minimum profile position $P_{min}$ may be calculated with the equation (19).

Further, after calculating the x-ray attenuation area S1 of the equivalent circular water phantom at the maximum profile position $P_{max}$ and the x-ray attenuation area S2 of the equivalent circular water phantom at the minimum profile position $P_{min}$, the equivalent circular water phantom at the maximum profile position $P_{max}$ may be converted into an equivalent elliptical water phantom of the same area, and the equivalent circular water phantom at the minimum profile position $P_{max}$ may be converted into an equivalent elliptical water phantom of the same area.

For example, supposing a1 and b1 represent the long axis and the short axis of the equivalent elliptical water phantom at the maximum profile position $P_{max}$ respectively, and supposing a2 and b2 represent the long axis and the short axis of the equivalent elliptical water phantom at the minimum profile position $P_{min}$ respectively, according to the area equivalent principle (i.e., the equivalent circular water phantom and the equivalent elliptical water phantom are of the same area), the following equations may hold:

$$S1 = \frac{\pi}{4} a1 \cdot b1 \tag{20}$$

$$S2 = \frac{\pi}{4} a2 \cdot b2 \tag{21}$$

$$\delta_{mean} = \frac{a1}{b1} = \frac{a2}{b2} \tag{22}$$

wherein, $\delta_{mean}$ may be calculated through the above equation (4).

Figures 6A, 6B:
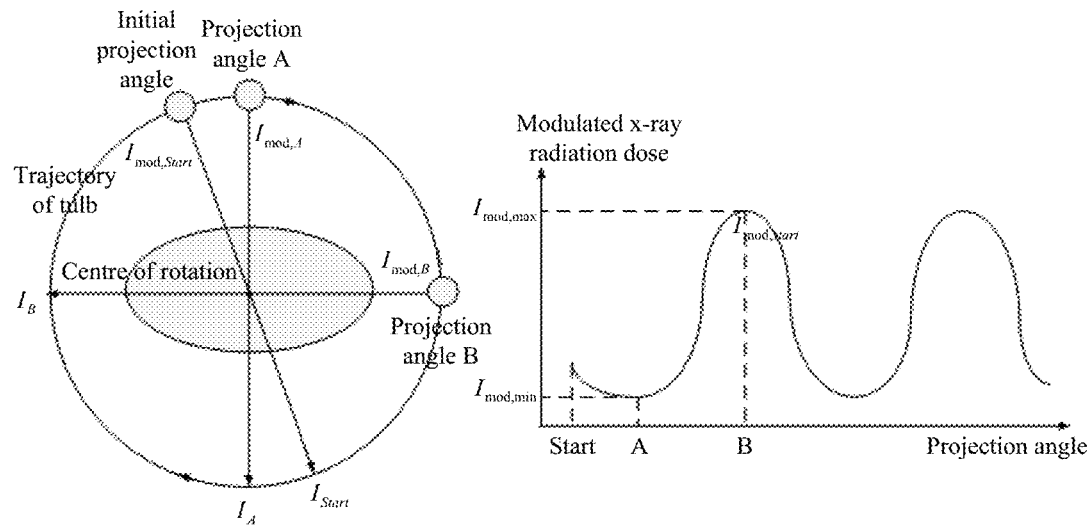
FIG. 6A schematically illustrates a diagram of modulating x-ray radiation dose of an equivalent water phantom in an example of the present disclosure.
FIG. 6B illustrates the curve of modulated x-ray radiation dose corresponding to the equivalent water phantom in FIG. 6A.

As a1 and b1 may be calculated through the equations (20) and (22), and a2 and b2 may be calculated through the equations (21) and (22), the equivalent circular water phantom at the maximum profile position $P_{max}$ may be converted into an equivalent elliptical water phantom having a long axis of a1 and a short axis of b1, and the equivalent circular water phantom at the minimum profile position $P_{min}$ may be converted into an equivalent elliptical water phantom having a long axis of a2 and a short axis of b2, as shown in FIG. 6A.

Figures 7A, 7B:
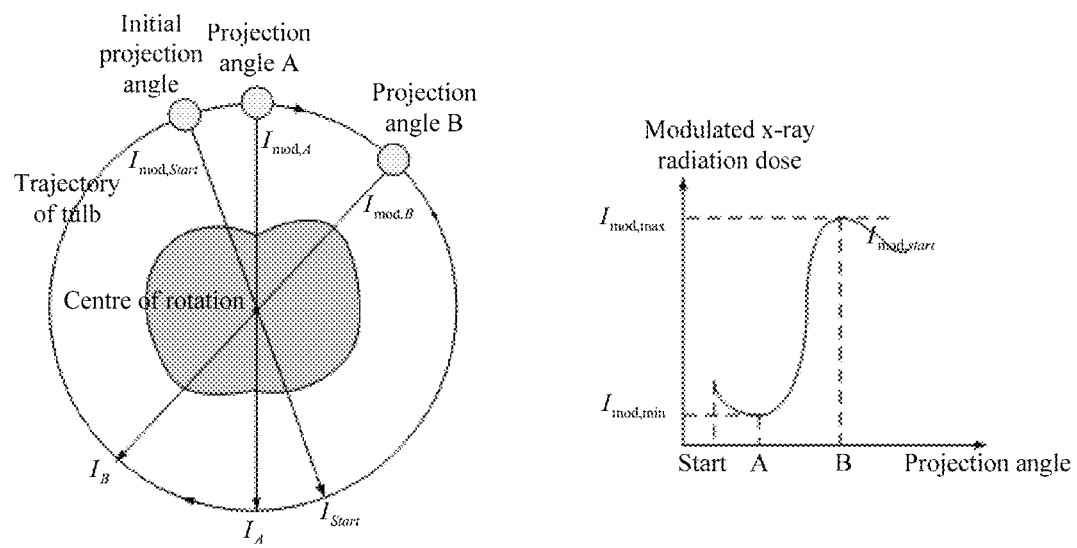
FIG. 7A schematically illustrates a diagram of modulating x-ray radiation dose of an equivalent water phantom in another example of the present disclosure.
FIG. 7B illustrates the curve of modulated x-ray radiation dose corresponding to the equivalent water phantom in FIG. 7A.

According to another example, the x-ray attenuation value for each of the projection angles j at the maximum profile position $P_{max}$ may be utilized to define an equivalent water phantom having a same area with the equivalent circular water phantom at the maximum profile position $P_{max}$, and the x-ray attenuation value for each of the projection angles j at the minimum profile position $P_{min}$ may be utilized to define an equivalent water phantom having a same area with the equivalent circular water phantom at the minimum profile position $P_{min}$, as shown in FIG. 7A.

For example, the x-ray attenuation value $\eta_{zPmax,j}$ for each of the projection angles at the maximum profile position $P_{max}$ may be calculated using the following equation:

$$\eta_{zPmax,j} = \overline{C_{mod,j}} * PA_{max,zPmax} \tag{23}$$

wherein, $\eta_{zPmax,j}$ represents the x-ray attenuation value for the $j^{th}$ projection angle at the maximum profile position $P_{max}$, $\overline{C_{mod,j}}$ represents the mean normalized x-ray attenuation value for the $j^{th}$ projection angle at each of Z positions within the overlapping sequence, which may be calculated through the equation (7), $PA_{max,zPmax}$ represents a maximum x-ray attenuation value in pilot image scanning of the XY scanning profile at the maximum profile position $P_{max}$.

Similarly, the x-ray attenuation value $\eta_{zP\ min,j}$ for each of the projection angles at the minimum profile position $P_{min}$ may be calculated using the following equation:

$$\eta_{zPmin,j} = \overline{C_{mod,j}} * PA_{max,zPmin} \tag{24}$$

wherein, $\eta_{zP\ min,j}$ represents the x-ray attenuation value for the $j^{th}$ projection angle at the minimum profile position $P_{min}$, $\overline{C_{mod,j}}$ represents the mean normalized x-ray attenuation value for the $j^{th}$ projection angle at each of Z positions within the overlapping sequence, which may be calculated through the equation (7), $PA_{max,zP\ min}$ represents a maximum x-ray attenuation value in pilot image scanning of the XY scanning profile at the minimum profile position $P_{min}$.

In the above equations (23) and (24), the mean normalized x-ray attenuation $\overline{C_{mod,j}}$ for the $j^{th}$ projection angle at each of Z positions within the overlapping sequence which is calculated according to the above equation (7), may be substituted with the mean normalized x-ray attenuation $\overline{B_{mod,j}}$ for the $j^{th}$ projection angle at each of Z positions within the overlapping sequence which is calculated according to the above equation (12). Thus, according to another example, the x-ray attenuation value $\eta_{zPmax,j}$ for each of the projection angles at the maximum profile position $P_{max}$ may be calculated using the following equation:

$$\eta_{zPmax,j} = \overline{B_{mod,j}} * D_{zPmax} \tag{25}$$

wherein, $\eta_{zPmax,j}$ represents the x-ray attenuation value for the $j^{th}$ projection angle at the maximum profile position $P_{max}$, $\overline{B_{mod,j}}$ represents the mean normalized x-ray attenuation value for the $j^{th}$ projection angle at each of Z positions within the overlapping sequence, which may be calculated using the equation (12), $D_{zP\ max}$ represents the diameter of the equivalent circular water phantom of the XY scanning profile at the maximum profile position $P_{max}$, that is the maximum equivalent circular water phantom diameter $D_{max}$.

Similarly, the x-ray attenuation value $\eta_{zP\ min,j}$ for each of the projection angles at the minimum profile position $P_{min}$ may be calculated using the following equation:

$$\eta_{zP\ min,j} = \overline{B_{mod,j}} * D_{zP\ min} \quad (26)$$

wherein, $\eta_{zP\ min,j}$ represents the x-ray attenuation value for the $j^{th}$ projection angle at the minimum profile position $P_{min}$, $\overline{B_{mod,j}}$ represents the mean normalized x-ray attenuation value for the $j^{th}$ projection angle at each of Z positions within the overlapping sequence, which may be calculated using the equation (12), $D_{zP\ min}$ represents the diameter of the equivalent circular water phantom of the XY scanning profile at the minimum profile position $P_{min}$, that is the minimum equivalent circular water phantom diameter $D_{min}$.

Finally, according to the proportional relation between the length of the x-ray attenuation path and the x-ray radiation dose for each of the projection angles, a maximum among x-ray radiation doses for different projection angles j of the equivalent water phantom at a maximum profile position may be determined as a maximum dose threshold value $T_{max}$, and a minimum among x-ray radiation doses for different projection angles j of the equivalent water phantom at a minimum profile position may be determined as a minimum dose threshold value $T_{min}$.

According to an example, an initial x-ray radiation dose may be set according to the maximum equivalent circular water phantom diameter $D_{max}$ at the maximum profile position $P_{max}$, the x-ray radiation dose for each of the projection angles j of the equivalent water phantom at the maximum profile position $P_{max}$ may be simulated, and then the maximum among the simulated x-ray radiation doses may be determined as the maximum x-ray dose threshold value $T_{max}$.

Similarly, an initial x-ray radiation dose may be set according to the minimum equivalent circular water phantom diameter $D_{min}$ at the minimum profile position $P_{min}$, and the x-ray radiation dose for each of the projection angles j of the equivalent water phantom at the minimum profile position $P_{min}$ may be simulated, and then a minimum among the simulated x-ray radiation doses may be determined as a minimum dose threshold value $T_{min}$.

Generally, the x-ray attenuation value of the X-ray irradiation may be described as follows:

$$I = I_0 \cdot \exp(-\mu l) \quad (27)$$

wherein, $I_0$ represents the original x-ray radiation dose of the X-ray irradiation, I represents the attenuated x-ray radiation dose after the original X-ray irradiation penetrates through the material having an x-ray attenuation coefficient of $\mu$ and a length l of the x-ray attenuation path.

It can be seen from the equation (27) that, the length of the x-ray attenuation path is proportional with the modulated x-ray radiation dose. Specifically, as shown in FIG. 6A and FIG. 7A, for a projection angle A having the shortest x-ray attenuation path, its modulated x-ray dose is the smallest, and for a projection angle B having the longest x-ray attenuation path, its modulated x-ray dose is the greatest. Further, the modulated x-ray dose for each of the projection angles are illustrated as modulated dose curves as shown in FIG. 6B and FIG. 7B.

In this way, through the above operation on the equivalent water phantom at the maximum profile position $P_{max}$, the simulated maximum modulated x-ray radiation dose may be derived as the maximum dose threshold value $T_{max}$, and through the above operation on the equivalent water phantom at the minimum profile position $P_{min}$, the simulated minimum modulated x-ray radiation dose may be derived as the minimum dose threshold value $T_{min}$.

Through the method for modulating x-ray radiation dose in CT scan according to the examples of the present disclosure, the x-ray attenuation information of a scan region of a subject is acquired according to a finished axial and/or helical scanning sequence of the subject, and then an optimized x-ray radiation dose modulation may performed based on the acquired x-ray attenuation information, so as to decrease the x-ray radiation dose absorbed by the subject and guarantee the noise consistency between reconstructed CT images for different scan regions of a same subject.

Figure 8:
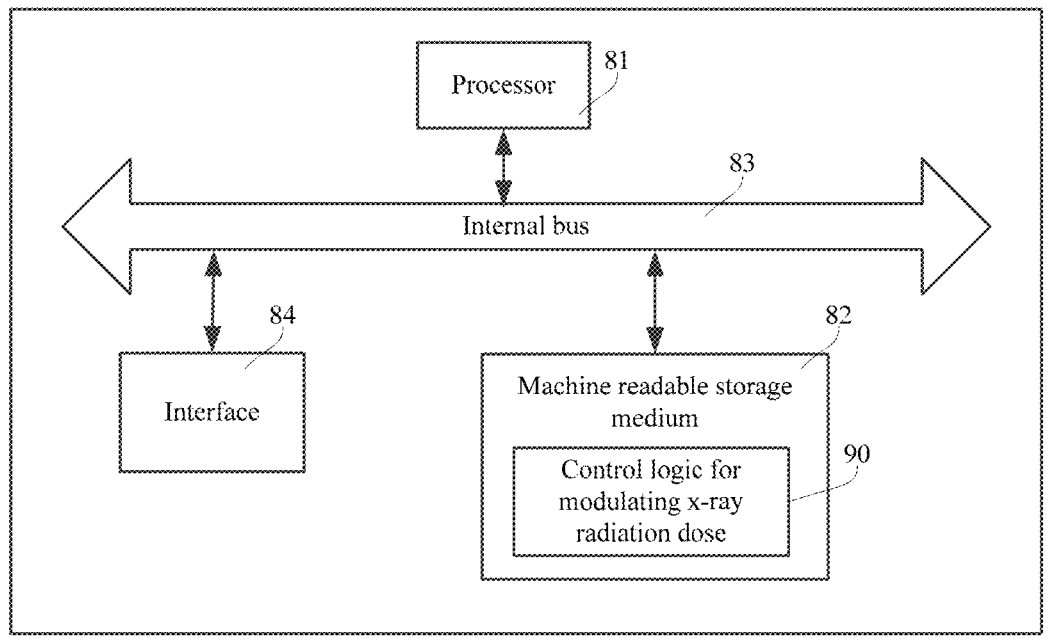
FIG. 8 schematically illustrates hardware structure of a device for modulating x-ray radiation dose in CT scan according to an example of the present disclosure.
Figure 9:
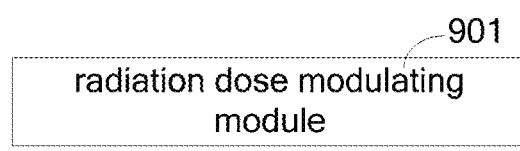
FIG. 9 schematically illustrates corresponding functional modules of a control logic which corresponds to the method for modulating x-ray radiation dose in CT scan as shown in FIG. 1 according to an example of the present disclosure.

Referring to FIG. 8, in correspondence with the above-described method, the present disclosure provides a device for modulating x-ray radiation dose in CT scan. As shown in FIG. 8, the device includes a processor 81 such as CPU and a machine readable storage medium 82, wherein the processor 81 and the machine readable storage medium 82 are connected with each other through an internal bus 83. In further examples, the device may also include an interface 84 so as to communicate with other devices or components.

In different examples, the machine readable storage medium 82 may include: Random Access Memory (RAM), volatile memory, non-volatile memory, flash memory, memory drive (such as hard disk drive), solid-state hard disk, other types of memory disk (such as optical disc and dvd) or similar types of storage medium or combinations of these.

Further, the machine readable storage medium 82 may be stored with machine-readable instructions of a control logic 90 for modulating x-ray radiation dose in CT scan. In terms of functionality, the control logic may include a x-ray radiation dose modulating module 901.

The x-ray radiation dose modulating module 901 is to acquire the x-ray attenuation information for each of the projection angles of the XY scanning profile at each of Z positions within the planned scanning sequence with respect to a scan region of a subject from data of a finished scanning sequence of the subject, and modulate the x-ray radiation dose for each of the projection angles of the XY scanning profile at each of Z positions within the planned scanning sequence according to the acquired x-ray attenuation information. Wherein, Z position represents a position in Z direction, Z direction represents a direction extending from head to foot of the subject or conversely, and the XY scanning profile represents a profile of the subject which is vertical to Z direction.

According to an example, if the planned scanning sequence is within the finished scanning sequence, the x-ray radiation dose modulating module 901 may specifically calculate the x-ray radiation dose for each of the projection angles of the XY scanning profile at each of Z positions zi within the planned scanning sequence according to the following equation:

$$I_{mod,zi,j} = \frac{M \cdot I_{mod,zi,start}}{\sum_{j=1}^{M} \sqrt{A_{max,zi,j}}} \cdot \sqrt{A_{max,zi,j}};$$

wherein, $I_{mod,zi,j}$ represents the x-ray radiation dose for the $j^{th}$ projection angle of the XY scanning profile at Z position zi, $I_{mod,zi,start}$ represents the initial x-ray radiation dose at Z position zi, M represents a quantity of projection angles, and j represents an index number of the $j^{th}$ projection angle, $A_{max,zi,j}$ represents a maximum x-ray attenuation value for the $j^{th}$ projection angle of the XY scanning profile at Z position zi and may be acquired from data of the finished scanning sequence.

According to another example, if the planned scanning sequence goes beyond the finished scanning sequence and the pilot image data of the planned scanning sequence has no abrupt change in Z direction, then the control logic 90 may further include a shape ratio determining module, which is to acquire shape ratio information of the XY scanning profile at each of Z positions within an overlapping sequence, and according to the acquired shape ratio information, determine whether the XY scanning profiles at different Z positions are similar. Wherein, the overlapping sequence represents a part of the planned scanning sequence which is overlapped with the finished scanning sequence.

In the above case, the x-ray radiation dose modulating module 901 may be further to: if it is determined that the XY scanning profiles at different Z positions are similar, calculate the x-ray radiation dose for each of the projection angles of the XY scanning profile at each of Z positions zi within the planned scanning sequence according to the following equation:

$$I_{mod,zi,j} = \begin{cases} T_{max}, & modv \geq T_{max} \\ modv = \frac{M \cdot I_{mod,zi,start}}{\sum_{j=1}^{M} \sqrt{A_{max,zi,j}}} \cdot \sqrt{A_{max,zi,j}}, & T_{min} \leq modv \leq T_{max} \\ T_{min}, & modv \leq T_{min} \end{cases};$$

wherein, $I_{mod,zi,j}$ represents the x-ray radiation dose for the $j^{th}$ projection angle of the XY scanning profile at Z position zi, $I_{mod,zi,start}$ represents the initial x-ray radiation dose of Z position zi, M represents a quantity of projection angles, j represents an index number of the $j^{th}$ projection angle, $A_{max,zi,j}$ represents a maximum x-ray attenuation value for the $j^{th}$ projection angle of the XY scanning profile at Z position zi, and if Z position zi is within the overlapping sequence, it may be directly acquired from data of the finished scanning sequence, otherwise, it may be calculated based on a maximum x-ray attenuation value for each of the projection angles of the XY scanning profile at another Z position which is closest to the Z position zi, $T_{max}$ and $T_{min}$ represent a maximum x-ray dose threshold value and a minimum x-ray dose threshold value respectively.

According to an example, the shape ratio determining module may specifically include:

a shape ratio information calculating sub-module, which is to calculate the ratio between the long axis and the short axis of the equivalent elliptical water phantom of the XY scanning profile at each of Z positions within the overlapping sequence as the shape ratio information, or calculate the x-ray attenuation deviation of each of Z positions within the overlapping sequence with respect to the whole overlapping sequence as the shape ratio information;

a variance calculating sub-module, which is to: calculate an arithmetic mean for the shape ratio information of the XY scanning profile at each of Z positions within the overlapping sequence, as a mean shape ratio information of the overlapping sequence; and calculate a variance with the shape ratio information of the XY scanning profile at each of Z positions within the overlapping sequence and the mean shape ratio information of the overlapping sequence, as a variance regarding shape ratio information of the overlapping sequence;

a determining sub-module, which is to determine whether the variance regarding shape ratio information is larger than a preset threshold or not, and if yes, it may indicate that the XY scanning profiles at different Z positions within the overlapping sequence are not similar, and if not, it may indicate that the XY scanning profiles at different Z positions within the overlapping sequence are similar.

In the case of calculating the x-ray attenuation deviation as the shape ratio information, the x-ray attenuation deviation of each of Z positions within the overlapping sequence with respect to the whole overlapping sequence may be calculated according to the following equation:

$$\Delta C_{mod,zi} = \frac{\sum_{j=1}^{M} \left| C_{mod,zi,j} - \frac{\sum_{i=1}^{NumZ} C_{mod,zi,j}}{NumZ} \right|}{M},$$

wherein, $\Delta C_{mod,zi}$ represents the x-ray attenuation deviation of each of Z positions zi within the overlapping sequence with respect to the whole overlapping sequence, M represents a quantity of projection angles, and j represents an index number of the $j^{th}$ projection angle, NumZ represents a quantity of Z positions within the overlapping sequence, and i represents an index number of the $i^{th}$ Z position, $C_{mod,zi,j}$ represents the normalized x-ray attenuation value for each of the projection angles at each of Z positions zi, which may be calculated by normalizing a maximum x-ray attenuation value for the $j^{th}$ projection angle of the XY scanning profile at Z position zi with a maximum x-ray attenuation value in pilot image scanning of the XY scanning profile at Z position zi or the diameter of the equivalent circular water phantom of the XY scanning profile at Z positions zi.

According to an example, in terms of functionality, the control logic 90 may further include:

a water phantom diameter determining module, which is to determine the diameter of the equivalent circular water phantom at each of Z positions within the planned scanning sequence based on pre-acquired pilot image data of the subject;

a profile position determining module, which is to select a maximum diameter and a minimum diameter of the diameters determined by the water phantom diameter determining module as the maximum equivalent circular water phantom diameter and the minimum equivalent circular water phantom diameter respectively, and determine Z position of a maximum equivalent circular water phantom diameter as a first profile position, and Z position of a minimum equivalent circular water phantom diameter as a second profile position;

a x-ray dose threshold value determining module, which is to convert the equivalent circular water phantom at the first profile position into a first equivalent water phantom of the same area, and convert the equivalent circular water phantom at the second profile position into a second equivalent water phantom of the same area, and according to the proportional relation of the length of the x-ray attenuation path and the x-ray radiation dose for each of the projection angles, determine a maximum x-ray radiation dose among the projection angles of the first equivalent water phantom as a maximum x-ray dose threshold value $T_{max}$, and determine a minimum x-ray radiation dose among the projection angles of the second equivalent water phantom as a minimum x-ray dose threshold value $T_{min}$.

According to an example, in the pilot image data of the subject, a set of slice data corresponding to a Z position within the planned scanning sequence may be $\{\mu_1 l_1, \mu_2 l_2, \ldots \mu_i l_i\}$, i=1, 2, 3, ..., N, and the water phantom diameter determining module may calculate the diameter of the equivalent circular water phantom at Z position through the following equation:

$$D_{water} = \frac{2}{\mu_{water}} \cdot \sqrt{\frac{S}{\pi}},$$

$$S = \sum_{i=1}^{N} (\mu_i l_i + \mu_{i+1} l_{i+1}) \cdot \Delta/2,$$

$$\Delta = R \cdot \frac{\theta}{N} \cdot g(h_{bed}, h_{center}),$$

wherein, $\mu_{water}$ represents the x-ray attenuation coefficient of water,

S represents the x-ray attenuation area of the equivalent circular water phantom of the set of slice data $\{\mu_1 l_1, \mu_2 l_2, \ldots \mu_i l_i\}$, i=1, 2, 3, ..., N, $\mu_i$ represents the mean x-ray attenuation coefficient on the $i^{th}$ detection channel, $l_i$, represents the length of the x-ray attenuation path on the $i^{th}$ detection channel, N represents a quantity of detection channels, $\Delta$ represents the distance between the centres of the adjacent detection units, R represents the radius of rotation, and $\theta$ represents the sector angle formed between the detection units and the bulb tube, $h_{bed}$ represents the distance between the scanning bed and the floor, $h_{center}$ represents the distance between the centre of rotation and the floor, and $g(h_{bed}, h_{center})$ represents a function modifying $\Delta$, and when the subject is located at the centre of rotation, $g(h_{bed}, h_{center})<1$; when the subject is located above the centre of rotation, $g(h_{bed}, h_{center})<1$; and when the subject is located below the centre of rotation, $g(h_{bed}, h_{center})>1$, and its specific value may be acquired by querying a table.

A process in which the device runs the control logic 90 for modulating x-ray radiation dose in CT scan will be described further below with respect to software implementation as an example. In this example, the disclosed control logic 90 should be understood as computer executable instructions stored in the machine readable storage medium 82. When the processor 81 on the disclosed device executes the control logic 90, the processor 81 carries out the following operations by invoking instructions of corresponding functional modules of control logic 90 stored on the machine readable storage medium 82:

acquiring x-ray attenuation information for each of the projection angles of the XY scanning profile at each of Z positions within a planned scanning sequence of a subject from data of a finished scanning sequence of the subject; and modulating, according to the acquired x-ray attenuation information, the x-ray radiation dose for each of the projection angles of the XY scanning profile at each of Z positions within the planned scanning sequence, wherein, Z position represents a position in Z direction, Z direction represents a direction extending from head to foot of the subject or conversely, and the XY scanning profile represents a profile of the subject which is vertical to Z direction.

According to an example, if the planned scanning sequence is within the finished scanning sequence, the instructions further cause the processor to perform the following operations:

acquiring a maximum x-ray attenuation value for each of the projection angles at each of Z positions within the planned scanning sequence from the data of the finished scanning sequence, and calculating the x-ray radiation dose for each of the projection angles of the XY scanning profile at each of Z positions zi within the planned scanning sequence with the following equation:

$$I_{mod,zi,j} = \frac{M \cdot I_{mod,zi,start}}{\sum_{j=1}^{M} \sqrt{A_{max,zi,j}}} \cdot \sqrt{A_{max,zi,j}};$$

wherein, $I_{mod,zi,j}$ represents the x-ray radiation dose for the $j^{th}$ projection angle of the XY scanning profile at Z position zi, $I_{mod,zi,start}$ represents the initial x-ray radiation dose of Z position zi, M represents a quantity of projection angles, and j represents an index number of the $j^{th}$ projection angle, and $A_{max,zi,j}$ represents a maximum x-ray attenuation value for the $j^{th}$ projection angle of the XY scanning profile at Z position zi and is acquired from the data of the finished scanning sequence.

According to an example, if the planned scanning sequence goes beyond the finished scanning sequence and the pilot image data of the planned scanning sequence has no abrupt change in Z direction, the instructions further cause the processor to perform the following operations:

acquiring shape ratio information of the XY scanning profile at each of Z positions in an overlapping sequence, wherein the overlapping sequence is a part of the planned scanning sequence which is overlapped with the finished scanning sequence, and determining whether the XY scanning profiles at different Z positions within the overlapping sequence are similar or not based on the acquired shape ratio information, and modulating, if the determination result is yes, the x-ray radiation dose for each of the projection angles of the XY scanning profile at each of Z positions within the planned scanning sequence according to the acquired x-ray attenuation information.

Further, the instructions cause the processor to perform the following operations:

acquiring a maximum x-ray attenuation value for each of the projection angles of the XY scanning profile at each of Z positions within the overlapping sequence from the data of the finished scanning sequence; and calculating a maximum x-ray attenuation value for each of the projection angles of the XY scanning profile at each of Z positions zout within the planned scanning sequence but not in the overlapping sequence according to the following equation:

$$A_{max,zout,j} = A_{max,zout-1,j} \frac{PA_{max,zout}}{PA_{max,zout-1}}$$

wherein, $A_{max,zout,j}$ represents a maximum x-ray attenuation value for the $j^{th}$ projection angle of the XY scanning profile at Z position zout;

$A_{max,zout-1,j}$ represents a maximum x-ray attenuation value for the $j^{th}$ projection angle of the XY scanning profile at Z position zout−1 which is closest to the Z position zout;

$PA_{max,zout}$ represents a maximum x-ray attenuation value in pilot image scanning of the XY scanning profile at Z position zout and is determined from a pre-acquired pilot image data of the subject;

$PA_{max,zout-1}$ represents a maximum x-ray attenuation value in pilot image scanning of the XY scanning profile at Z position zout−1 and is determined from a pre-acquired pilot image data of the subject.

Further, the instructions cause the processor to perform the following operations:

calculating the x-ray radiation dose for each of the projection angles of the XY scanning profile at each of Z positions zi within the planned scanning sequence through the following equation:

$$I_{mod,zi,j} = \begin{cases} T_{max}, & mod\nu \geq T_{max} \\ mod\nu = \frac{M \cdot I_{mod,zi,start}}{\sum_{j=1}^{M}\sqrt{A_{max,zi,j}}} \cdot \sqrt{A_{max,zi,j}}, & T_{min} \leq mod\nu \leq T_{max} \\ T_{min}, & mod\nu \leq T_{min} \end{cases};$$

wherein, $I_{mod,zi,j}$ represents the x-ray radiation dose for the $j^{th}$ projection angle of the XY scanning profile at Z position zi, $I_{mod,zi,start}$ represents the initial x-ray radiation dose of Z position zi, M represents a quantity of projection angles, and j represents an index number of the $j^{th}$ projection angle, $A_{max,zi,j}$ represents a maximum x-ray attenuation value for the $j^{th}$ projection angle of the XY scanning profile at Z position zi, $T_{max}$ and $T_{min}$ represent a maximum x-ray dose threshold value and a minimum x-ray dose threshold value respectively, mod ν represents an intermediate x-ray value for comparing with $T_{max}$ and $T_{min}$ to determine $I_{mod,zi,j}$.

According to examples of the disclosure, the shape ratio information of the XY scanning profile at each of Z positions within the overlapping sequence may be one of the following:

the ratio between the long axis and the short axis for the equivalent elliptical water phantom of the XY scanning profile at each of Z positions within the overlapping sequence, or the x-ray attenuation deviation of each of Z positions within the overlapping sequence with respect to the whole overlapping sequence.

Further, according to an example, the x-ray attenuation deviation of each of Z positions within the overlapping sequence with respect to the whole overlapping sequence is calculated through the following equation:

$$\Delta C_{mod,zi} = \frac{\sum_{j=1}^{M}\left|C_{mod,zi,j} - \frac{\sum_{i=1}^{NumZ}C_{mod,zi,j}}{NumZ}\right|}{M},$$

wherein, $\Delta C_{mod,zi}$ represents the x-ray attenuation deviation of each of Z positions zi within the overlapping sequence with respect to the whole overlapping sequence, M represents a quantity of projection angles, j represents an index number of the $j^{th}$ projection angle, NumZ represents a quantity of Z positions within the overlapping sequence, i represents an index number of the $i^{th}$ Z position, $C_{mod,zi,j}$ represents the normalized x-ray attenuation value for each of the projection angles at each of Z positions zi, which is calculated by normalizing a maximum x-ray attenuation value for the $j^{th}$ projection angle of the XY scanning profile at Z position zi with a maximum x-ray attenuation value in pilot image scanning of the XY scanning profile at Z position zi or the diameter of the equivalent circular water phantom of the XY scanning profile at Z position zi.

Further, the instructions cause the processor to perform the following operations:

calculating an arithmetic mean for the shape ratio information of the XY scanning profile at each of Z positions within the overlapping sequence, as a mean shape ratio information of the overlapping sequence;

calculating a variance with the shape ratio information of the XY scanning profile at each of Z positions within the overlapping sequence and the mean shape ratio information of the overlapping sequence, as a variance regarding shape ratio information of the overlapping sequence; and determining whether the variance regarding shape ratio information is larger than a preset threshold value or not, and if yes, it indicates that the XY scanning profiles at different Z positions within the overlapping sequence are not similar, and if no, it indicates that the XY scanning profiles at different Z positions within the overlapping sequence are similar.

Further, the instructions cause the processor to perform the following operations:

calculating the diameter of equivalent circular water phantom at each of Z positions within the planned scanning sequence based on a pre-acquired pilot image data of the subject;

determining a maximum and a minimum among the calculated diameters as a maximum equivalent circular water phantom diameter and a minimum equivalent circular water phantom diameter respectively, determining the Z position of a maximum equivalent circular water phantom diameter as a first profile position and the Z position of a minimum equivalent circular water phantom diameter as a second profile position;

converting the equivalent circular water phantom at the first profile position into a first equivalent water phantom of the same area, and converting the equivalent circular water phantom at the second profile position into a second equivalent water phantom of the same area; and according to the proportional relation between the length of the x-ray attenuation path and the x-ray radiation dose for each of the projection angles, determining a maximum of the x-ray radiation doses for projection angles of the first equivalent water phantom as a maximum x-ray dose threshold value $T_{max}$, and determining a minimum of the x-ray radiation doses for projection angles of the second equivalent water phantom as a minimum x-ray dose threshold value $T_{min}$.

The above are only preferred examples of the present disclosure is not intended to limit the disclosure within the spirit and principles of the present disclosure, any changes made, equivalent replacement, or improvement in the protection of the present disclosure should contain within the range.

The methods, processes and units described herein may be implemented by hardware (including hardware logic circuitry), software or firmware or a combination thereof. The term 'processor' is to be interpreted broadly to include a processing unit, ASIC, logic unit, or programmable gate array etc. The processes, methods and functional units may all be performed by the one or more processors; reference in this disclosure or the claims to a 'processor' should thus be interpreted to mean 'one or more processors'.

Further, the processes, methods and functional units described in this disclosure may be implemented in the form of a computer software product. The computer software product is stored in a storage medium and comprises a plurality of instructions for making a processor to implement the methods recited in the examples of the present disclosure.

The figures are only illustrations of an example, wherein the units or procedure shown in the figures are not necessarily essential for implementing the present disclosure. Those skilled in the art will understand that the units in the device in the example can be arranged in the device in the examples as described, or can be alternatively located in one or more devices different from that in the examples. The units in the examples described can be combined into one module or further divided into a plurality of sub-units.

Although the flowcharts described show a specific order of execution, the order of execution may differ from that which is depicted. For example, the order of execution of two or more blocks may be changed relative to the order shown. Also, two or more blocks shown in succession may be executed concurrently or with partial concurrence. All such variations are within the scope of the present disclosure.

Throughout the present disclosure, the word "comprise", or variations such as "comprises" or "comprising", will be understood to imply the inclusion of a stated element, integer or step, or group of elements, integers or steps, but not the exclusion of any other element, integer or step, or group of elements, integers or steps.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A method for modulating x-ray radiation dose in CT scan, the method comprising:

acquiring, from data of a finished scanning sequence of a subject, x-ray attenuation information for each of the projection angles of the XY scanning profile at each of Z positions within a planned scanning sequence of the subject; and modulating, according to the acquired x-ray attenuation information, an x-ray radiation dose for each of the projection angles of the XY scanning profile at each of Z positions within the planned scanning sequence;

wherein Z position includes a position in Z direction from head to foot of the subject or conversely, the XY scanning profile represents a profile of the subject which is vertical to Z direction and the finished scanning sequence of the subject includes a scanning sequence for a same scan region of the same subject which has been finished before current time;

wherein when the planned scanning sequence goes beyond the finished scanning sequence and pilot image data of the planned scanning sequence has no abrupt change in Z direction, the method further includes:

acquiring shape ratio information of the XY scanning profile at each of Z positions in an overlapping sequence, wherein the overlapping sequence is a part of the planned scanning sequence which is overlapped with the finished scanning sequence, and determining whether the XY scanning profiles at different Z positions within the overlapping sequence are similar to each other based on the acquired shape ratio information, when the XY scanning profiles at different Z positions within the overlapping sequence are determined as being similar to each other, modulating the x-ray radiation dose for each of the projection angles of the XY scanning profile at each of Z positions within the planned scanning sequence according to the acquired x-ray attenuation information.

2. The method of claim 1, wherein, when the planned scanning sequence is within the finished scanning sequence:

said acquiring the x-ray attenuation information for each of the projection angles of the XY scanning profile at each of Z positions within the planned scanning sequence includes: acquiring, from the data of the finished scanning sequence, a maximum x-ray attenuation value for each of the projection angles at each of Z positions within the planned scanning sequence, and said modulating the x-ray radiation dose for each of the projection angles of the XY scanning profile at each of Z positions within the planned scanning sequence includes: calculating the x-ray radiation dose for each of the projection angles of the XY scanning profile at each of Z positions zi within the planned scanning sequence with the following equation:

$$I_{mod,zi,j} = \frac{M \cdot I_{mod,zi,start}}{\sum_{j=1}^{M} \sqrt{A_{max,zi,j}}} \cdot \sqrt{A_{max,zi,j}};$$

wherein, $I_{mod,zi,j}$ represents an x-ray radiation dose for the $j^{th}$ projection angle of the XY scanning profile at Z position zi, $I_{mod,zi,start}$ represents an initial x-ray radiation dose of Z position zi, M represents a quantity of projection angles, and j represents an index number of the $j^{th}$ projection angle, and $A_{max,zi,j}$ represents a maximum x-ray attenuation value for the $j^{th}$ projection angle of the XY scanning profile at Z position zi and is acquired from the data of the finished scanning sequence.

3. The method of claim 1, said acquiring the x-ray attenuation information for each of the projection angles of the XY scanning profile at each of Z positions within the planned scanning sequence, includes:

acquiring a maximum x-ray attenuation value for each of the projection angles of the XY scanning profile at each of Z positions within the overlapping sequence from the data of the finished scanning sequence; and calculating a maximum x-ray attenuation value for each of the projection angles of the XY scanning profile at each of Z positions zout within the planned scanning sequence but not in the overlapping sequence according to the following equation:

$$A_{max,zout,j} = A_{max,zout-1,j} \frac{PA_{max,zout}}{PA_{max,zout-1}}$$

wherein, $A_{max,zout,j}$ represents a maximum x-ray attenuation value for the $j^{th}$ projection angle of the XY scanning profile at Z position zout;

$A_{max,zout-1,j}$ represents a maximum x-ray attenuation value for the $j_{th}$ projection angle of the XY scanning profile at Z position zout−1 which is closest to the Z position zout;

$PA_{max,zout}$ represents a maximum x-ray attenuation value in pilot image scanning of the XY scanning profile at Z position zout and is determined from a pre-acquired pilot image data of the subject; and $PA_{max,zout-1}$ represents a maximum x-ray attenuation value in pilot image scanning of the XY scanning profile at Z position zout−1 and is determined from pre-acquired pilot image data of the subject.

4. The method of claim 3, wherein, said modulating the x-ray radiation dose for each of the projection angles of the XY scanning profile at each of Z positions within the planned scanning sequence, includes:

calculating the x-ray radiation dose for each of the projection angles of the XY scanning profile at each of Z positions zi within the planned scanning sequence through the following equation:

$$I_{mod,zi,j} = \begin{cases} T_{max}, & modv \geq T_{max} \\ modv = \frac{M \cdot I_{mod,zi,start}}{\sum_{j=1}^{M} \sqrt{A_{max,zi,j}}} \cdot \sqrt{A_{max,zi,j}}, & T_{min} \leq modv \leq T_{max} \\ T_{min}, & modv \leq T_{min} \end{cases};$$

wherein, $I_{mod,zi,j}$ represents an x-ray radiation dose for the $j^{th}$ projection angle of the XY scanning profile at Z position zi, $I_{mod,zi,start}$ represents an initial x-ray radiation dose of Z position zi, M represents a quantity of projection angles, and j represents an index number of the $j^{th}$ projection angle, $A_{max,zi,j}$ represents a maximum x-ray attenuation value for the $j^{th}$ projection angle of the XY scanning profile at Z position zi, $T_{max}$ and $T_{min}$ represent a maximum x-ray dose threshold value and a minimum x-ray dose threshold value respectively, and mod v represents an intermediate x-ray value for comparing with $T_{max}$ and $T_{min}$ to determine $I_{mod,zi,j}$.

5. The method of claim 1, wherein, the shape ratio information of the XY scanning profile at each of Z positions within the overlapping sequence is one of the following:

the ratio between a long axis and a short axis for the equivalent elliptical water phantom of the XY scanning profile at each of Z positions within the overlapping sequence, or an x-ray attenuation deviation of each of Z positions within the overlapping sequence with respect to the whole overlapping sequence.

6. The method of claim 5, wherein, the x-ray attenuation deviation of each of Z positions within the overlapping sequence with respect to the whole overlapping sequence is calculated through the following equation:

$$\Delta C_{mod,zi} = \frac{\sum_{j=1}^{M} \left| C_{mod,zi,j} - \frac{\sum_{i=1}^{NumZ} C_{mod,zi,j}}{NumZ} \right|}{M},$$

wherein, $\Delta C_{mod,zi}$ represents an x-ray attenuation deviation of each of Z positions zi within the overlapping sequence with respect to the whole overlapping sequence, M represents a quantity of projection angles, j represents an index number of the $j^{th}$ projection angle, NumZ represents a quantity of Z positions within the overlapping sequence, i represents an index number of the $i^{th}$ Z position, $C_{mod,zi,j}$ represents a normalized x-ray attenuation value for each of the projection angles at each of Z positions zi, which is calculated by normalizing the maximum x-ray attenuation value for the $j^{th}$ projection angle of the XY scanning profile at Z position zi with a maximum x-ray attenuation value in pilot image scanning of the XY scanning profile at Z position zi or the diameter of the equivalent circular water phantom of the XY scanning profile at Z position zi.

7. The method of claim 1, wherein, said determining whether the XY scanning profiles at different Z positions within the overlapping sequence are similar to each other based on the acquired shape ratio information, includes:

calculate an arithmetic mean for the shape ratio information of the XY scanning profile at each of Z positions within the overlapping sequence, as a mean shape ratio information of the overlapping sequence;

calculating a variance with the shape ratio information of the XY scanning profile at each of Z positions within the overlapping sequence and the mean shape ratio information of the overlapping sequence, as a variance regarding shape ratio information of the overlapping sequence; and determining whether the variance regarding shape ratio information is larger than a preset threshold value or not, wherein if the variance is determined as being larger than the preset threshold value, it is indicated that the XY scanning profiles at different Z positions within the overlapping sequence are not similar, and if the variance is determined as being not larger than the preset threshold value, it is indicated that the XY scanning profiles at different Z positions within the overlapping sequence are similar.

8. The method of claim 4, further including:
calculating the diameter of equivalent circular water phantom at each of Z positions within the planned scanning sequence based on pre-acquired pilot data of the subject;
determining a maximum diameter and a minimum diameter among the calculated diameters as a maximum equivalent circular water phantom diameter and a minimum equivalent circular water phantom diameter respectively,
determining the Z position of the maximum equivalent circular water phantom diameter as a first profile position and the Z position of the minimum equivalent circular water phantom diameter as a second profile position;
converting the equivalent circular water phantom at the first profile position into a first equivalent water phantom of the same area, and converting the equivalent circular water phantom at the second profile position into a second equivalent water phantom of the same area; and
according to the proportional relation between the length of the x-ray attenuation path and the x-ray radiation dose for each of the projection angles, determining the maximum of the x-ray radiation doses for projection angles of the first equivalent water phantom as the maximum x-ray dose threshold value $T_{max}$, and determining the minimum of the x-ray radiation doses for projection angles of the second equivalent water phantom as the minimum x-ray dose threshold value $T_{min}$.

9. A device for modulating x-ray radiation dose in CT scan, the device comprising:
a processor configured to execute machine readable instructions corresponding to a control logic for modulating x-ray radiation dose in CT scan, the machine readable instructions being stored on a storage medium and, when executed, causing the processor to:
acquire, from data of a finished scanning sequence of a subject, x-ray attenuation information for each of the projection angles of the XY scanning profile at each of Z positions within a planned scanning sequence of the subject; and
modulate, according to the acquired x-ray attenuation information, an x-ray radiation dose for each of the projection angles of the XY scanning profile at each of Z positions within the planned scanning sequence;
wherein Z position represents a position in Z direction from head to foot of the subject or conversely, the XY scanning profile represents a profile of the subject which is vertical to Z direction and the finished scanning sequence of the subject includes a scanning sequence for a same scan region of the same subject which has been finished before current time;
wherein when the planned scanning sequence goes beyond the finished scanning sequence and pilot image data of the planned scanning sequence has no abrupt change in Z direction, the instructions further cause the processor to:
acquire shape ratio information of the XY scanning profile at each of Z positions in an overlapping sequence, wherein the overlapping sequence is a part of the planned scanning sequence which is overlapped with the finished scanning sequence, and
determine whether the XY scanning profiles at different Z positions within the overlapping sequence are similar to each other based on the acquired shape ratio information,
when the XY scanning profiles at different Z positions within the overlapping sequence are determined as being similar to each other, modulate the x-ray radiation dose for each of the projection angles of the XY scanning profile at each of Z positions within the planned scanning sequence according to the acquired x-ray attenuation information.

10. A device for modulating x-ray radiation dose in CT scan, the device comprising:
a processor configured to execute machine readable instructions corresponding to a control logic for modulating x-ray radiation dose in CT scan, the machine readable instructions being stored on a storage medium and, when executed, causing the processor to perform the method for modulating x-ray radiation dose in CT scan, wherein said modulating the x-ray radiation dose for each of the projection angles of the XY scanning profile at each of Z positions within the planned scanning sequence includes:
calculating the x-ray radiation dose for each of the projection angles of the XY scanning profile at each of Z positions zi within the planned scanning sequence with the following equation:

$$I_{mod,zi,j} = \frac{M \cdot I_{mod,zi,start}}{\sum_{j=1}^{M} \sqrt{A_{max,zi,j}}} \cdot \sqrt{A_{max,zi,j}} \ ;$$

wherein, $I_{mod,zi,j}$ represents an x-ray radiation dose for the $j^{th}$ projection angle of the XY scanning profile at Z position zi,
$I_{mod,zi,start}$ represents an initial x-ray radiation dose of Z position zi,
M represents a quantity of projection angles, and j represents an index number of the $j^{th}$ projection angle, and
$A_{max,zi,j}$ represents a maximum x-ray attenuation value for the $j^{th}$ projection angle of the XY scanning profile at Z position zi and is acquired from the data of the finished scanning sequence.

11. The device of claim 9, the instructions further cause the processor to:
acquire a maximum x-ray attenuation value for each of the projection angles of the XY scanning profile at each of Z positions within the overlapping sequence from the data of the finished scanning sequence; and
calculate a maximum x-ray attenuation value for each of the projection angles of the XY scanning profile at each of Z positions zout within the planned scanning sequence but not in the overlapping sequence according to the following equation:

$$A_{max,zout,j} = A_{max,zout-1,j} \frac{PA_{max,zout}}{PA_{max,zout-1}}$$

wherein, $A_{max,zout,j}$ represents a maximum x-ray attenuation value for the $j^{th}$ projection angle of the XY scanning profile at Z position zout;

$A_{max,zout-1,j}$ represents a maximum x-ray attenuation value for the $j^{th}$ projection angle of the XY scanning profile at Z position zout-1 which is closest to the Z position zout;

$PA_{max,zout}$ represents a maximum x-ray attenuation value in pilot image scanning of the XY scanning profile at Z position zout and is determined from a pre-acquired pilot image data of the subject;

$PA_{max,zout-1}$ represents a maximum x-ray attenuation value in pilot image scanning of the XY scanning profile at Z position zout-1 and is determined from pre-acquired pilot image data of the subject.

12. The device of claim 11, wherein, the instructions further cause the processor to:
calculate the x-ray radiation dose for each of the projection angles of the XY scanning profile at each of Z positions zi within the planned scanning sequence through the following equation:

$$I_{mod,zi,j} = \begin{cases} T_{max}, & \mathrm{mod}v \geq T_{max} \\ \mathrm{mod}v = \dfrac{M \cdot I_{mod,zi,start}}{\sum_{j=1}^{M} \sqrt{A_{max,zi,j}}} \cdot \sqrt{A_{max,zi,j}}, & T_{min} \leq \mathrm{mod}v \leq T_{max} \\ T_{min}, & \mathrm{mod}v \leq T_{min} \end{cases} ;$$

wherein, $I_{mod,zi,j}$ represents an x-ray radiation dose for the $j^{th}$ projection angle of the XY scanning profile at Z position zi, $I_{mod,zi,start}$ represents an initial x-ray radiation dose of Z position zi, M represents a quantity of projection angles, and j represents an index number of the $j^{th}$ projection angle, $A_{max,zi,j}$ represents a maximum x-ray attenuation value for the $j^{th}$ projection angle of the XY scanning profile at Z position zi, $T_{max}$ and $T_{min}$ represent a maximum x-ray dose threshold value and a minimum x-ray dose threshold value respectively, mod v represents an intermediate x-ray value for comparing with $T_{max}$ and $T_{min}$ to determine $I_{mod,zi,j}$.

13. The device of claim 9, wherein, the shape ratio information of the XY scanning profile at each of Z positions within the overlapping sequence is one of the following:
the ratio between a long axis and a short axis for the equivalent elliptical water phantom of the XY scanning profile at each of Z positions within the overlapping sequence, or
an x-ray attenuation deviation of each of Z positions within the overlapping sequence with respect to the whole overlapping sequence.

14. The device of claim 13, wherein, the instructions further cause the processor to:
calculate the x-ray attenuation deviation of each of Z positions within the overlapping sequence with respect to the whole overlapping sequence through the following equation:

$$\Delta C_{mod,zi} = \dfrac{\sum_{j=1}^{M} \left| C_{mod,zi,j} - \dfrac{\sum_{i=1}^{NumZ} C_{mod,zi,j}}{NumZ} \right|}{M},$$

wherein, $\Delta C_{mod,zi}$, represents an x-ray attenuation deviation of each of Z positions zi within the overlapping sequence with respect to the whole overlapping sequence, M represents a quantity of projection angles, j represents an index number of the $j^{th}$ projection angle, NumZ represents a quantity of Z positions within the overlapping sequence, i represents an index number of the $i^{th}$ Z position, $C_{mod,zi,j}$ represents the normalized x-ray attenuation value for each of the projection angles at each of Z positions zi, which is calculated by normalizing the maximum x-ray attenuation value for the $j^{th}$ projection angle of the XY scanning profile at Z position zi with a maximum x-ray attenuation value in pilot image scanning of the XY scanning profile at Z position zi or the diameter of the equivalent circular water phantom of the XY scanning profile at Z position zi.

15. The device of claim 9, wherein, the instructions further cause the processor to:
calculate an arithmetic mean for the shape ratio information of the XY scanning profile at each of Z positions within the overlapping sequence, as a mean shape ratio information of the overlapping sequence;
calculate a variance with the shape ratio information of the XY scanning profile at each of Z positions within the overlapping sequence and the mean shape ratio information of the overlapping sequence, as a variance regarding shape ratio information of the overlapping sequence; and
determine whether the variance regarding shape ratio information is larger than a preset threshold value or not, wherein if the variance is determined as being larger than the preset threshold value, it is indicated that the XY scanning profiles at different Z positions within the overlapping sequence are not similar, and if the variance is determined as being not larger than the preset threshold value, it is indicated that the XY scanning profiles at different Z positions within the overlapping sequence are similar.

16. The device of claim 12, wherein, the instruction further cause the processor to:
calculate the diameter of equivalent circular water phantom at each of Z positions within the planned scanning sequence based on a pre-acquired pilot image data of the subject;
determine a maximum diameter and a minimum diameter among the calculated diameters as a maximum equivalent circular water phantom diameter and a minimum equivalent circular water phantom diameter respectively,
determine the Z position of the maximum equivalent circular water phantom diameter as a first profile position and the Z position of the minimum equivalent circular water phantom diameter as a second profile position;
convert the equivalent circular water phantom at the first profile position into a first equivalent water phantom of the same area, and convert the equivalent circular water phantom at the second profile position into a second equivalent water phantom of the same area; and
according to the proportional relation between the length of the x-ray attenuation path and the x-ray radiation dose for each of the projection angles, determine the maximum of the x-ray radiation doses for projection angles of the first equivalent water phantom as the maximum x-ray dose threshold value $T_{max}$, and determine the minimum of the x-ray radiation doses for projection angles of the second equivalent water phantom as the minimum x-ray dose threshold value $T_{min}$.

* * * * *